United States Patent
Cedillo et al.

(10) Patent No.: US 9,034,272 B2
(45) Date of Patent: May 19, 2015

(54) APPARATUS FOR SYNTHESIZING OLIGONUCLEOTIDES AND METHODS OF USE

(75) Inventors: Isaiah E. Cedillo, Vista, CA (US); Max N. Moore, Encinitas, CA (US); Francis J. Ring, Oceanside, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 699 days.

(21) Appl. No.: 13/375,697

(22) PCT Filed: May 28, 2010

(86) PCT No.: PCT/US2010/036599
§ 371 (c)(1),
(2), (4) Date: Jan. 23, 2012

(87) PCT Pub. No.: WO2010/141361
PCT Pub. Date: Dec. 9, 2010

(65) Prior Publication Data
US 2012/0107181 A1 May 3, 2012

Related U.S. Application Data

(60) Provisional application No. 61/184,743, filed on Jun. 5, 2009.

(51) Int. Cl.
*B01J 8/02* (2006.01)
*B01J 19/00* (2006.01)
*C12M 1/00* (2006.01)

(52) U.S. Cl.
CPC ............... *B01J 19/0046* (2013.01); *B01J 8/02* (2013.01); *C12M 1/00* (2013.01); *B01J 2219/0029* (2013.01); *B01J 2219/00418* (2013.01); *B01J 2219/0059* (2013.01); *B01J 2219/00596* (2013.01); *B01J 2219/00695* (2013.01); *B01J 2219/00698* (2013.01); *B01J 2219/00722* (2013.01)

(58) Field of Classification Search
CPC .................................... B01J 8/02; C12M 1/00
USPC ....................................... 422/201; 435/289.1
See application file for complete search history.

(56) References Cited

U.S. PATENT DOCUMENTS

| 2,999,060 | A * | 9/1961 | Teitel ............................. 376/212 |
| 5,736,654 | A | 4/1998 | Dubois |
| 2001/0043883 | A1 | 11/2001 | Chalk |
| 2003/0023171 | A1 | 1/2003 | Sato et al. |
| 2004/0247500 | A1 * | 12/2004 | Ashe et al. ..................... 422/200 |

(Continued)

OTHER PUBLICATIONS

Lyttle et al., "A Phosphate Bound Universal Linker for SNA Synthesis." Nucleosides, Nucleotides and Nucleic Acids (1999) 18(8):1809-1824.

(Continued)

*Primary Examiner* — Walter D Griffin
*Assistant Examiner* — Huy-Tram Nguyen
(74) *Attorney, Agent, or Firm* — Casimir Jones, S.C.

(57) ABSTRACT

The present invention relates to apparatus and methods for synthesizing oligonucleotides wherein a reaction zone has a variable volume based on the position of a piston, and the piston is adjusted to control the amount of headspace above solid support in the reaction zone. Methods and apparatus that limit the size or existence of the headspace are described.

16 Claims, 5 Drawing Sheets

(56) References Cited

U.S. PATENT DOCUMENTS

2005/0002831 A1* 1/2005 Ashe et al. .................... 422/106
2007/0117099 A1 5/2007 Engelhardt et al.

OTHER PUBLICATIONS

International Search Report for application PCT/US10/36599 dated Jul. 19, 2010.

* cited by examiner

APPARATUS FOR SYNTHESIZING OLIGONUCLEOTIDES AND METHODS OF USE

REFERENCE TO RELATED APPLICATION

This application is a U.S. National Phase filing under 35 U.S.C. 371 claiming priority to International Application No. PCT/US2010/036599, filed May 28, 2010; which is the non-provisional claiming priority to U.S. Provisional 61/184,743, filed Jun. 5, 2009; each of which is incorporated herein by reference in its entirety.

FIELD OF THE INVENTION

The present invention is directed to reactors, and more specifically to synthesizers for manufacturing oligomeric compounds such as oligonucleotides.

BACKGROUND

Oligonucleotides are polymers of nucleotides and are formed by sequentially linking a number of nucleotides together in a chain. These chains may have less than twenty nucleotides, but in some cases may have several hundred nucleotides. Oligonucleotides are useful for, inter alia, hybridizing to complementary DNA or RNA. The interactions between oligonucleotides and modified oligonucleotides with complementary RNA is being exploited in a number of therapeutic, diagnostic, and research applications. Consequently, oligonucleotides may be useful in, for example, pharmaceutical research, as well as for certain medical testing.

Oligonucleotides may be synthesized in a laboratory environment using a series of steps. During this synthesis, nucleotides are attached in a chain in a desired order. The series of steps taken when adding a nucleotide is referred to as a synthetic cycle, and may involve: removal of a dimethoxytrityl group (detritylation); attachment of the desired nucleotide phosphoramidite to the location previously held by the dimethoxytrityl group (coupling); blocking of any sites where the dimethoxytrityl group was not replaced by the desired nucleotide phosphoramidite (capping); and stabilizing the resultant structures (oxidation). These steps may be conducted manually, or by automatic synthesizers that have been developed that facilitate the process.

Essentially, each of the steps in the synthetic cycle involves a reagent that reacts with the oligonucleotide undergoing synthesis. For the synthetic cycle described above, a different reagent may be used in each of the steps of detritylation, coupling, capping and oxidation. It will be appreciated that for each nucleotide that is added to the chain, numerous reagents may be used. To provide more efficient reactions during the synthesis, it is desirable to reduce the degree to which reagents are allowed to mix with other reagents used in adjacent steps.

The synthesis may be conducted in a laboratory using a type of reactor called a synthesizer. Synthesizers include a reaction zone in which the synthesis occurs, and this reaction zone typically includes a frit, or filter, at the top and bottom of the reaction zone. A reagent flows through the top frit and into the reaction zone where the reaction takes place. The excess reagent and any products of the reaction then exit the reaction zone through the bottom frit. By introducing reagents serially through the top frit and removing them through the bottom frit, the degree of interaction between the reagents may be decreased as compared to earlier systems.

Oligonucleotide synthesis typically involves the use of a solid support, which may consist of a granular polymeric material, to which the first nucleotide is attached; other nucleotides then are added sequentially to form a chain. Following the addition of the final nucleotide, the chain is separated from the solid support. The solid support provides a foundation on which the oligonucleotide may be built, and the larger size of the solid support helps to avoid the loss of the oligonucleotide chain as different reagents are processed through the synthesizer during the synthetic cycles. In this regard, the granules of the solid support typically are larger than the pores of the bottom frit, so that the solid support does not exit the reaction zone as the excess reagents flow through the reaction zone and out the bottom frit.

In a reaction zone containing a solid support, there may exist a space between the solid support and the top frit. This space, called the "headspace," provides a volume in which a reagent is able to mix with the reagent used in the preceding step in the synthesis process. In order to reduce this interaction, additional solid support may be used to fill the volume of the reaction zone and thereby reduce the volume available for mixing of the reagents.

Nevertheless, some solid supports may swell or contract when exposed to different reagents during the synthetic process. Thus, the volume of the solid support undergoing the reactions varies during the synthetic process. Some previously-known synthesizers have attempted to address this variation by varying the axial compression applied by the top frit. In such systems, the top frit is attached to a piston which moves up and down within the reaction zone of the synthesizer. In such a system, a predetermined pressure is maintained hydraulically by adjustment of the location of a hydraulic piston within the reaction zone.

The foregoing method of adjusting the top frit location does not provide for optimal conditions within the reactor for synthesizing oligonucleotides involving dozens of reactions and significant changes in pressure, volume and other conditions. Additionally, because numerous, vastly different pressures may occur during oligonucleotide synthesis, there may be no direct relationship between the pressure within the reaction zone and the amount of headspace that forms during any given step. Accordingly, previously-known systems are unable to provide oligonucleotide synthesis while also minimizing or eliminating headspace.

Moreover, while headspace may be reduced by applying a sufficiently large pressure to a system designed to maintain a constant pressure, such a pressure would need to be at least as large as the maximum pressure observed during the synthesis process. In a synthesis process involving a wide range of pressures, however, the continued application of high pressure during a step involving only a low pressure may cause undesirable compression of the solid support. Accordingly, the effectiveness of the system may be compromised and the desired reactions may not occur as desired.

Accordingly, there is a need for apparatus and methods for synthesizing oligonucleotides that facilitate efficient reactions by reducing or eliminating the headspace.

There is also a need for apparatus and methods for synthesizing oligonucleotides that reduce or eliminate headspace without causing undue compaction of the contents of the synthesizer.

There is yet further a need for apparatus and methods for synthesizing oligonucleotides that reduce or eliminate headspace for a system that experiences dynamic changes in pressure and/or volume when undergoing multiple reactions.

SUMMARY OF THE INVENTION

Apparatus and methods are provided for synthesizing oligonucleotides that facilitate efficient reactions by reducing or eliminating headspace.

In accordance with the principles of the present invention, apparatus and methods are provided for synthesizing oligonucleotides that reduce or eliminate the headspace without causing undue compaction to the contents of the synthesizer.

Apparatus and methods are also provided for synthesizing oligonucleotides that reduce or eliminate headspace for a system that experiences dynamic changes in pressure and volume when undergoing multiple reactions.

These and other needs are met by apparatus and methods for synthesizing wherein the volume of the synthesizer reaction zone is dynamically adjusted to compensate for variations in the conditions of the material within the vessel.

The apparatus disclosed herein can also be used to prepare any manner of polymer or oligomeric compound using monomer subunits capable of being elongated using solid phase methods. The term "oligomeric compound" therefore includes oligonucleotides, oligonucleotide analogs and oligonucleosides. It also includes polymers having non-naturally occurring or modified nucleosides (wherein modified nucleosides include those wherein the base and/or the sugar have been replaced or modified as is routine in the art). In certain embodiments, oligomeric compounds comprise a plurality of monomer subunits independently selected from naturally occurring nucleosides, non-naturally occurring nucleosides and modified nucleosides.

In some embodiments of the invention, a reactor is provided comprising a vessel configured to contain a solid support, the vessel having an inlet and an outlet; a piston operatively arranged to reciprocate with the vessel; an actuator coupled to the piston; and a monitor configured to at least periodically adjust the actuator during a synthesis process to maintain the piston substantially in contact with the solid support.

In some embodiments, a solid support changes volume in response to exposure to reagents at different steps (stages) of the synthesis process. These changes in volume are determined from empirical testing prior to the synthesis. The monitor then is programmed to adjust the actuator during the synthesis process such that the piston reciprocates within the vessel thereby defining the volume of the reaction zone to be substantially the same as the volume of the solid support. Accordingly, the system preferably maintains the piston substantially in contact with the solid support, with little to no headspace.

In other embodiments, the reactor also comprises a pressure sensor and the monitor is configured to sense the output of the pressure sensor and to adjust the actuator in response. These embodiment are particularly beneficial if the pressures of the different reactions are predetermined, and are correlated to known volumes. Accordingly, the piston may be moved in discrete steps to correspond to the volume of the solid support associated with the measured pressure.

In some such embodiments, the reactor also comprises a contact sensor and the monitor is configured to sense the output of the contact sensor and to adjust the actuator in response. In these embodiments, no prior knowledge of the volume fluctuations corresponding to the reaction steps is required. Instead, the piston may extend into the vessel until contact is made with the solid support. Once such contact is established, further movement may be restricted. These systems may be further configured such that if the contact sensor experiences a predetermined amount of contact or resistance, the piston may be retracted. Accordingly, the piston's movement may be adjusted so that it maintains contact with the solid support, while avoiding compaction of the solid support as the volume of the solid support increases.

In still other such embodiments, the reactor also comprises a sensor configured to generate a signal corresponding to a detection of a headspace and the monitor is configured to sense the output of the sensor and to adjust the actuator to reduce or eliminate the headspace. In these embodiment, no prior knowledge of fluctuations on the volume of the solid support corresponding to the reaction stages is required.

In some embodiments of the invention, a synthesizer is provided that comprises a vessel configured to contain a granular polymeric material, the vessel having an inlet and an outlet, the vessel configured to receive fluid through the inlet; a piston operatively arranged to reciprocate with the vessel; an actuator coupled to the piston; and a monitor configured to at least periodically adjust the actuator during the synthesis process to maintain the piston within a predetermined distance from the polymeric material.

In some such embodiments, the polymeric material changes volume in response to exposure to reagents at different stages of the synthesis process. These changes in volume are determined from empirical testing prior to the synthesis. The monitor is then programmed to adjust the actuator during the synthesis process such that the piston reciprocates within the vessel thereby defining the volume of the vessel to be substantially the same as the volume of the polymeric material. Accordingly, the system can maintain the piston within a predetermined distance from the polymeric material, thereby controlling the amount of headspace.

In other such embodiments, the reactor also comprises a pressure sensor and the monitor is configured to sense the output of the pressure sensor and to adjust the actuator in response. These embodiments are particularly beneficial if the pressures of the different reactions are predetermined, and are correlated to known volumes. Accordingly, the piston may be moved in discrete steps to correspond to the volume of the polymeric material that is associated with the measured pressure.

In yet other such embodiments, the reactor also comprises a sensor configured to generate an output corresponding to the detection of a predetermined distance between the piston and the granular polymeric material. The monitor is configured to sense the output of the sensor and to adjust the actuator in response. These embodiments may be beneficial when the volume of the solid support corresponding to the reaction stages is known. Instead, the piston may move inward until it is within a predetermined distance from the polymeric material.

DETAILED DESCRIPTION OF THE INVENTION

Figure 1:
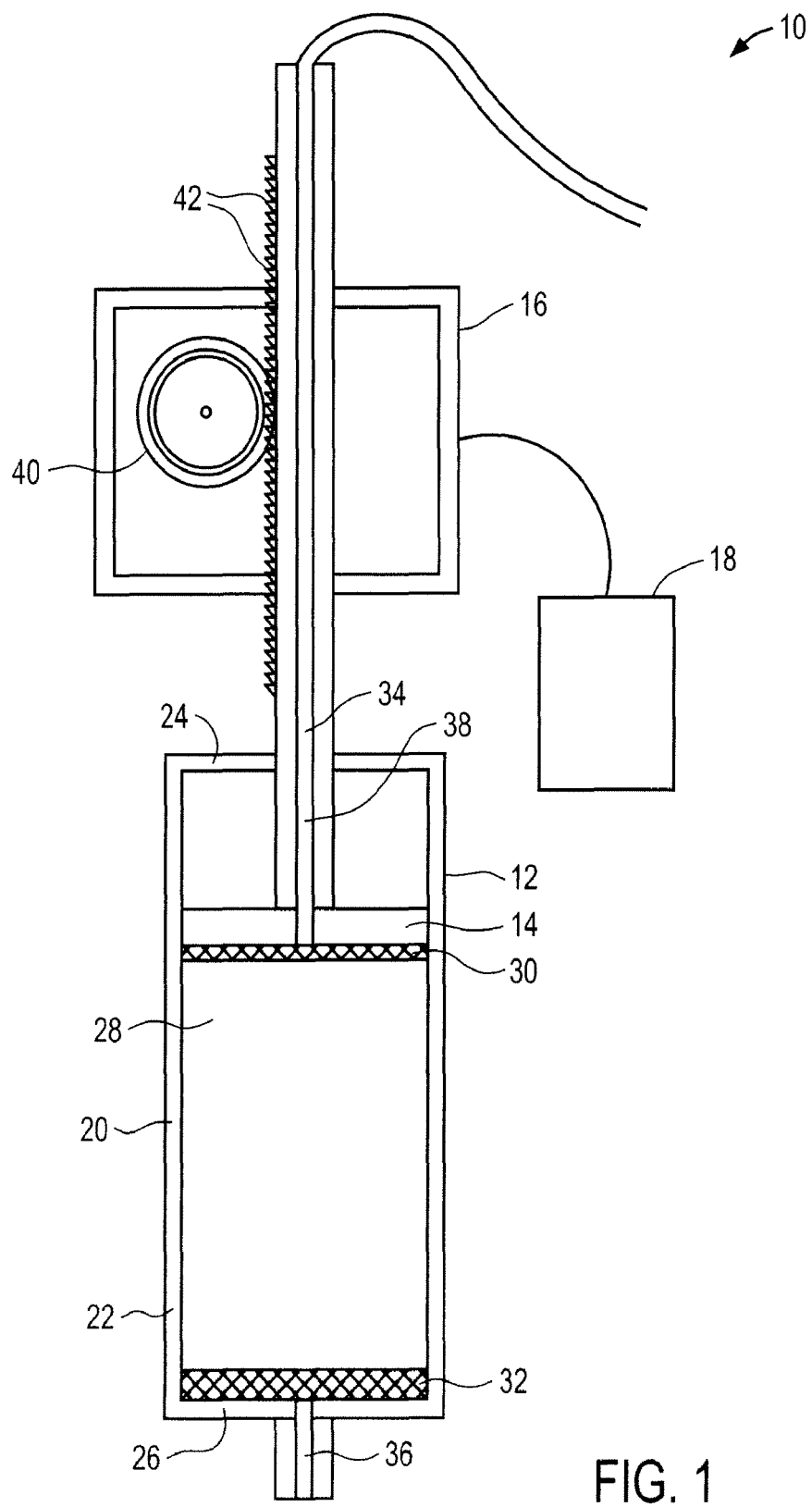
FIG. 1 is a schematic depiction of an embodiment of reactor in accordance with the present invention.

Referring to FIG. 1, an embodiment of the present invention is disclosed in which a synthesizer may be preprogrammed to adjust the volume of a reaction zone to correspond to the volume of a solid support within the reaction zone. Reactor 10 comprises vessel 12, piston 14, actuator 16, and monitor 18.

Vessel 12 have a cross-section that is circular, square, rectangular, triangular, ovate, irregular, or any number of other shapes. In a preferred embodiment, vessel 12 includes cylinder 20 having circular cross-section formed of sidewall 22, as well as top 24 and bottom 26. One of skill in the art will appreciate that top 24 is optional and is not necessary in this embodiment. Piston 14 reciprocates within cylinder 20 and together these components define reaction zone 28.

Reaction zone 28 may vary in volume, wherein the volume of reaction zone 28 decreases as piston 14 is extended into vessel 12, and volume of reaction zone 28 increases as piston 14 is retracted from vessel 12. Frit 30 is attached to piston 14 and frit 32 is located at or near bottom 26. Frits 30 and 32 each are preferably dimensioned to allow desired fluids to pass therethrough, but have sufficiently small openings or passageways to restrict solid support from passing into or clogging the openings in the frit. Suitable solid supports may include swellable or non-swellable granules and may include controlled pore glass (CPG), macroporous polystyrene (MPPS) or other commercially available solid supports known to those of skill in the art. Thus, for example, solid supports may have an average particle diameter of 1 µm-1 cm, and frit 32 preferably has openings smaller than the minimum diameter size for the selected solid support.

Vessel has inlet 34 and outlet 36 through which fluids may pass. Such fluids include solvents and reagents used for the synthesis of oligonucleotides. Inlet 34 preferably includes passageway 38 that connects to a manifold inside piston 14, such that the fluid is released from a plurality of openings and passes uniformly from piston 14 through frit 30 and into reaction zone 28. In a preferred embodiment, reactor 10 is in fluid communication with one or more reagents via passageway 38.

The position of piston 14 within vessel 12 is controlled by actuator 16. In one embodiment, actuator 16 comprises gear 40 that engages teeth 42 operatively coupled to piston 14. As gear 40 rotates, piston 14 is selectively extended or retracted within vessel 12. It will be appreciated that numerous other types of actuators are known in the art and may be used in place of actuator 16. Other suitable actuators include but are not limited to hydraulic actuators, pneumatic actuators and those having a worm gear.

Monitor 18 is operatively coupled to actuator 16, and in some embodiments may be integrated into that device. Monitor 18 communicates with actuator 16 and may direct actuator 16 to adjust the position of piston 14. Monitor 18 may comprise a microprocessor, logic processor, or other programmable device. In the embodiment described with respect to FIG. 1, monitor 18 is equipped with a memory, such as RAM or ROM, to store data related to the volume of solid support at various steps in the process of synthesizing oligonucleotides. Monitor 18 also may include an input device and display to receive and respond to user input or automated feedback, as discussed in greater detail below.

In practice, the chemical reactions occurring during the synthesis of oligonucleotides within reactor 10 is similar to the synthesis in known devices, in that a volume of solid support is maintained in a reaction zone and is subjected to various reactions (such as detritylation, coupling, capping and oxidation). However, reactor 10 advantageously adjusts piston 14 so as to maintain piston 14 substantially in contact with the solid support thereby reducing or eliminating headspace within the reaction zone. One manner in which this is accomplished is described in reference to FIG. 2.

Figure 2:
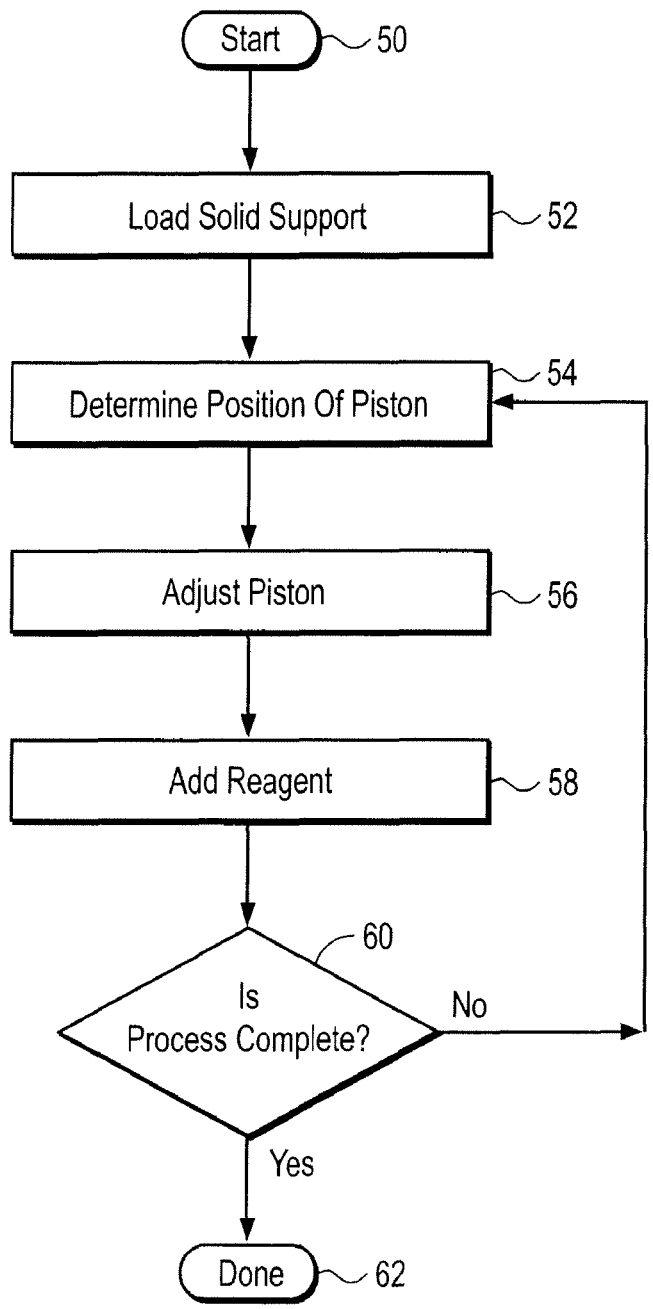
FIG. 2 is a flow chart describing a method of using a reactor in accordance with the present invention.

FIG. 2 depicts an illustrative series of steps that may be used with reactor 10 to efficiently synthesize oligonucleotides in accordance with one aspect of the present invention. This procedure requires prior knowledge of the types of reactions that occur within the reactor, as well as the changes in volume of the solid support occurring during each synthesis stage. For example, in the synthesis of oligonucleotides, a solid support may be placed in the column of a synthesizer. The solid support then is exposed to a series of reactions involved in a synthetic cycle, during which time the solid support may expand or contract when exposed to different reagents. The degree to which the solid support expands or contracts when exposed to a particular reagent may be different during the first synthetic cycle than it would be when exposed to the same reagent during the twentieth cycle in the synthesis of an oligonucleotide. Accordingly, it is preferable to have a database of information that includes the degree of expansion or contraction of a solid support that takes into account the reagent and the point in the process at which the reaction occurs.

Referring to FIG. 2, reactor 10 is programmed by inputting the type of solid support that will be used, along with the desired sequence of the oligonucleotide to be synthesized. As described below, reactor 10 proceeds through each synthesis stage until the oligonucleotide is synthesized, and then cleaves the oligonucleotide from the solid support.

At step 50, a user first inputs the type and amount of solid support, as well as the desired oligonucleotide sequence. At step 52, a measured amount of solid support is loaded into vessel 12 of synthesizer 10.

At step 54, the monitor determines which reagent to add to vessel 12, and then determines the position of the piston based on both the reagent that is added and the point of the process at which the reaction occurs. This determination may involve simply retrieving empirical data for a prior reaction from a database, or may involve a computation made from prior empirical test results.

At step 56, monitor 18 sends a signal to actuator 16 to move piston 14 to the desired location. This movement may occur in a stepwise fashion, wherein the entire movement occurs in a short amount of time, or it may be more gradual, wherein the movement occurs more slowly and may be concurrent with the addition of the reagent. In step 58, reagent is added to vessel 12 via inlet 34.

At step 60, the monitor evaluates whether the process is complete typically, for example, by determining whether the elapsed time for the synthesis stage has met a preprogrammed value. If so, the method proceeds to step 62, which indicates completion of the process. Otherwise, the method returns to steps 54 and 56 and the position of the piston is adjusted based on the next reagent used in the process and corresponding positional data for the piston determined or derived from the database.

It will be appreciated that the order of these steps may be varied as desired by a user. For example, it may be desirable to perform step 58 prior to step 56 so that a certain reagent is added prior to any movement of piston 14. Accordingly, the steps in FIG. 2 should be understood to be just one of a variety of methods which may be practiced in accordance with the present invention.

Further appreciation of the method described in FIG. 2 may be provided by example of a single synthetic cycle of the process of synthesizing an oligonucleotide. To begin, a desired oligonucleotide sequence is programmed into monitor 18, along with the starting solid support. Programming of monitor 18 may include inputting a particular reagent to be used for a step of the synthetic cycle, the flow rate of a reagent, the volume of a reagent, the temperature of a reagent, and/or the duration that a reagent will flow into the reaction zone. Then, the measured amount of solid support is added to the vessel, corresponding to step 52. At step 54, monitor 18 sends a signal to actuator 16 to lower piston 14 to the point at which the piston will make contact with the solid support as determined by the amount of solid support that a user inputted into monitor 18.

At step 56, actuator 16 extends piston 14 into vessel 12. Then, the first step in the synthesis cycle occurs, which may be the addition of dichloroacetic acid (DCA) in a solvent for the detritylation step through inlet 34 at step 58. At step 60, the monitor determines that the process is not complete, and then returns to step 54 where it then determines the position of the piston for the next stage of the cycle, which may be washing the solid support with solvent to complete the detritylation step. At step 56, piston 14 may be adjusted by actuator 16 based on a signal received from monitor 18. At step 58, the solvent is introduced through inlet 34 and exits through outlet 36 for a predetermined amount of time. Then, the process proceeds to step 60, wherein the monitor determines whether the process is complete.

Once a determination is made that the process is not complete, the process returns to step 54. This loop may continue for the coupling step, the capping step and the oxidation step. After the synthesis cycle is complete, monitor 18 determines whether another nucleotide will be added to the oligonucleotide chain. If so, the process continues to repeat. Once the oligonucleotide has been synthesized, the method may proceed to step 62 to indicate that the process is complete.

One advantage of the apparatus and method described above is that the movement of actuator 16 and/or piston 14 may be programmed as part of the actions taken by an automated synthesizer. As such, an automated synthesizer which is programmable to add different reagents to a column may be modified in accordance with this invention to control the movement of a piston such that the position and/or movement of the piston may be programmed for each of the numerous steps of the synthesis process.

It will be appreciated that it would be advantageous to control the movement of a piston in order to maintain the piston substantially in contact with a solid support even if there was no prior knowledge of the degree (if any) that the solid support would change in volume when exposed to a reagent. Other embodiments of the present invention address this need. In some embodiments, a synthesizer in accordance with the present invention includes a sensor or other mechanism for generating a feedback signal that is communicated to the monitor to dynamically control the position of a piston.

Figure 3:
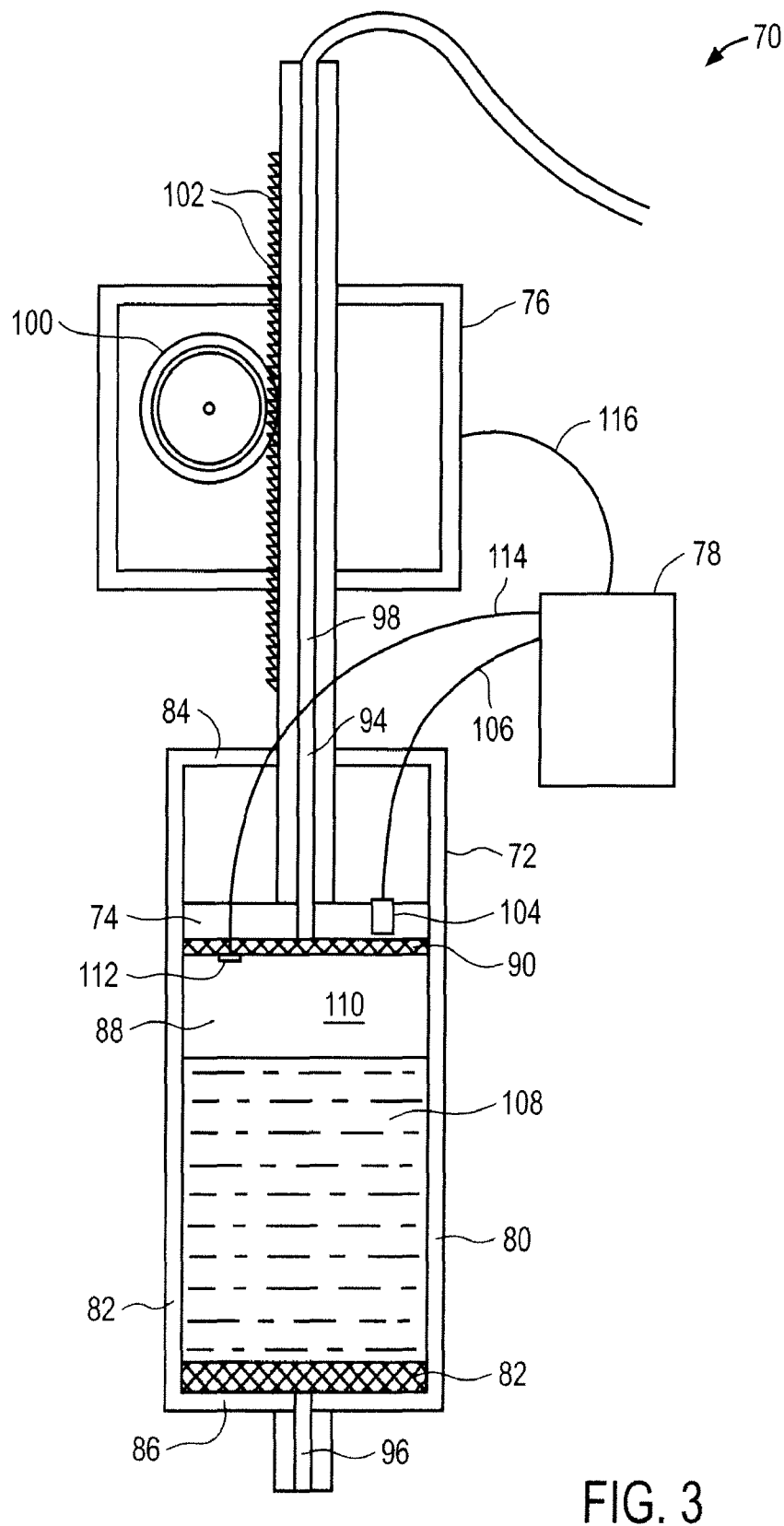
FIG. 3 is a schematic depiction of another embodiment of reactor in accordance with the present invention.

FIG. 3 describes an embodiment of the present invention that includes a feedback mechanism. Reactor 70 is similar to reactor 10, but includes a feedback mechanism. In this regard, reactor 70 includes the following components, which generally have similar descriptions of their counterparts in reactor 10: vessel 72, piston 74, actuator 76, monitor 78, cylinder 80, sidewall 82, top 84, bottom 86, reaction zone 88, frit 90, frit 92, inlet 94, outlet 96, passageway 98, gear 100, and teeth 102.

In addition to the above components, reactor 70 further comprises sensor 104 that is in communication with monitor 78. In this embodiment, sensor 104 communicates with monitor 78 via signals passed along wire 106. In other embodiments, signals may be communicated via a fiber optic cable, wirelessly via electronic signals or otherwise, or through other known communication media.

One notable difference between the components of reactor 10 and reactor 70 is that monitor 78 of reactor 70 need not operate based on preprogrammed information that was calculated or obtained from empirical testing, though optionally it may. Instead, monitor 78 receives feedback from sensor 104 that is used to evaluate whether and to what degree to move piston 74. Accordingly, reactor 70 may be used for reactions in which no prior test results have been stored.

Sensor 104 is in communication with vessel 72, wherein sensor 104 is specifically configured to sense or detect conditions within vessel 72. Sensor 104 may comprise one or more of an optical sensor, an acoustic sensor, a magnetic sensor, an energy ray sensor, a mechanical sensor, a fiber optic sensor, a conductivity sensor, or a pH sensor. Moreover, although sensor 104 in reactor 70 is coupled to piston 74, in other embodiments it may be located elsewhere, such as in sidewall 82. One such example of a sensor located in a sidewall would be one or more lasers located on one side of a vessel, and a corresponding series of receptors located on the other side of the vessel, each receptor adapted to sense the presence of the laser emission. The reception of a laser emission would indicate the presence of headspace in the reaction zone.

Headspace 110 is illustrated in FIG. 3. In particular, in FIG. 3 solid support 108 is disposed within vessel 72, and specifically within reaction zone 88. Piston 74 is depicted in a position in which it is not in contact with solid support 108, and instead is separated by a distance that is a fraction of the distance between piston 74 and bottom 86. Accordingly, headspace 110 is the volume of space between the top of solid support 108 and the bottom of piston 74.

Headspace 110 often will be filled with a fluid, and in particular a reagent. As a reagent is introduced through inlet 94, it comes into contact with solid support 108, which impedes the free fluid flow. Accordingly, some fluid may accumulate at the top of solid support 108 as other fluid slowly moves through solid support 108 prior to exiting through outlet 96.

Sensor 104 may be adapted to indicate the presence of a headspace using one or more of a variety of methods as indicated above. In FIG. 3, sensor 104 illustratively comprises a sonar transponder that detects the presence of space between piston 74 and solid support 108.

Alternatively, sensor 104 may use a laser, acoustic transducer, or a contact sensor comprising a linear array of detectors that are covered by a focusing lens and flanked by red, green, and blue LEDs for illumination. Additionally, electromechanical sensors that utilize piezoelectric elements may be used to indicate contact between the sensor and solid support; and strain gauge sensors may be coupled to the piston to indicate an amount of load applied to the solid support. It will be appreciated that these sensor configurations are merely exemplary and are not intended to limit the scope of the invention in any way.

Reactor 70 may comprise one or more additional sensors. For example, sensor 112 may be disposed on the bottom of piston 74 and may be configured to detect contact pressure between piston 74 and solid support 108. Sensor 112 preferably communicates detections to monitor 78. This communication may occur via an electrical transmission along wire 114, or through other media as indicated above. Likewise, monitor 78 may communicate with actuator 76 via various media, including electrical signals sent via wire 116.

Figure 4:
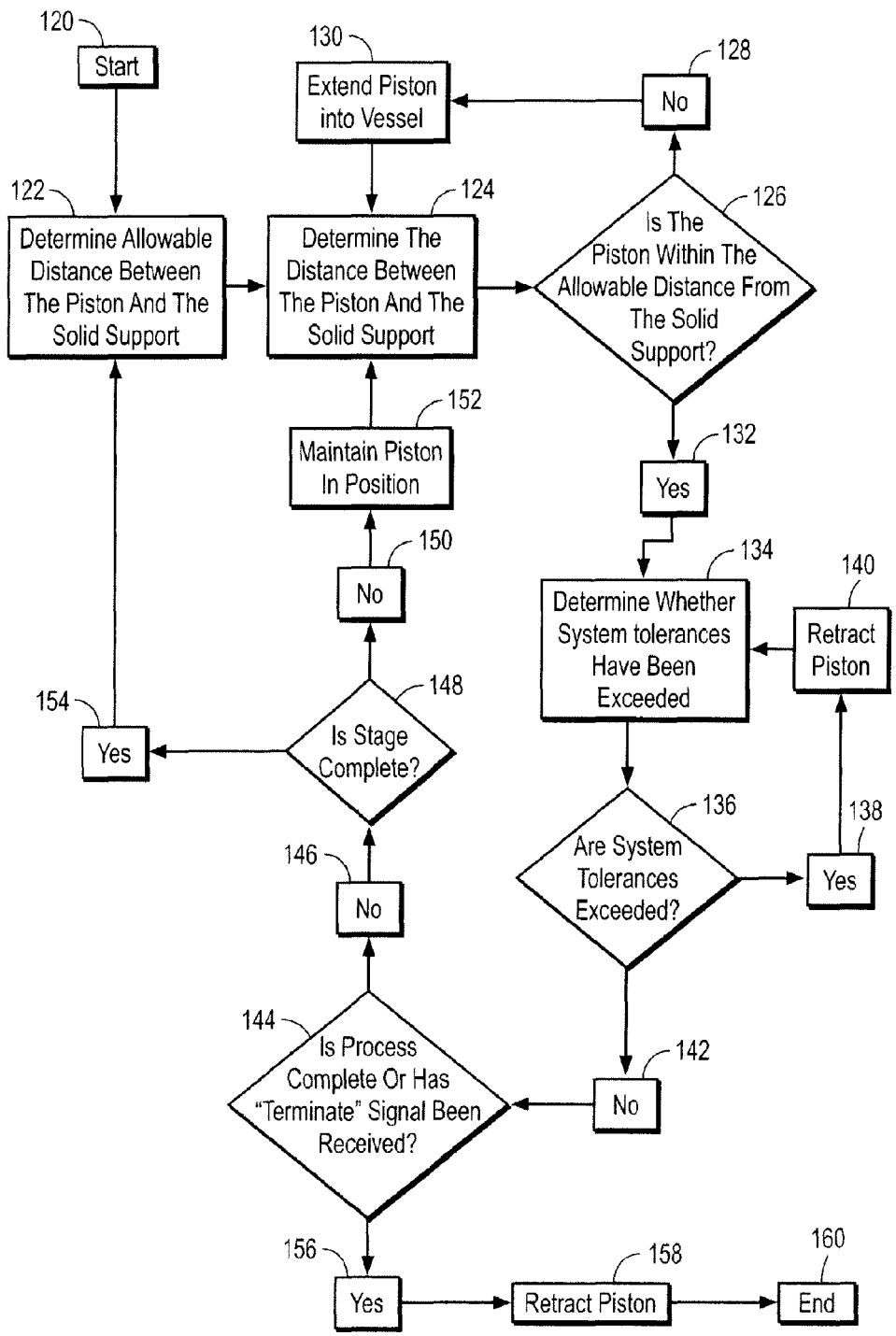
FIG. 4 is a flow chart describing a method of using a reactor in accordance with the present invention.

A method of using the feedback system of reactor 70 is described with respect to FIG. 4. It will be appreciated that this method and variations thereof may apply to other embodiments of the present invention, and therefore the description in reference to reactor 70 should in no way be considered limiting.

The initial point, step 120, may be at any point in the synthesis process, but is conveniently chosen to be at the initiation of the process or at the initiation of a stage in the process (i.e., prior to the introduction of a different reagent). For purposes of this explanation, it will be assumed that step 120 occurs during the synthesis process and prior to the stage in which reagent R is introduced into reaction zone 88 via passageway 98.

At step 122, a determination is made as to the allowable distance between piston 74 and solid support 108. This distance may be represented as a fixed amount, such as 5 mm, or it may be represented as a variable amount, such as 5% of the length of reaction zone 88. In the latter case, it will be clear that the further piston 74 extends into vessel 72, the shorter the length of reaction zone 88 becomes and, therefore, the allowable distance is decreased proportionally. Of course, other representations of the distance may be selected, such as a distance of zero, representing contact between piston 74 (or frit 90) and solid support 108, which may represent a zero headspace condition. Another representation of the distance may be found from a combined approach, such as a distance of 3 mm plus 3% of the length of reaction zone 88. This determination may be made by a user and communicated to monitor 78. In other embodiments the determination may be made in a different manner, such as by monitor 78 based on historical data, computations, systems tolerances, or other factors.

At step 124, a determination is made of the distance between piston 74 and solid support 108. This distance may be correlated to the volume of headspace 110 based on the geometry of vessel 72. The determination of this distance is provided based on detections by sensor 104. In the embodiment described in regard to FIG. 3, sensor 104 comprises a sonar transponder that detects the presence of a depth between piston 74 and solid support 108. Sensor 104 may operate by measuring the time to receive an echo of a transmitted sound pulse, wherein a longer time period indicates a great distance for given fluid conditions. Sensor 104 communicates distance data to monitor 78.

Once the distance between piston 74 and solid support 108 is determined, monitor 78 compares that distance to the allowable distance at step 126. In the event that the distance between piston 74 and solid support 108 is greater than the allowable distance, a "no" response results, as shown in step 128. In response, monitor 78 communicates a signal to actuator 76 to extend piston 74.

Actuator 76 then may activate gear 100 to engage teeth 102 of piston 74 and cause piston 74 to extend into vessel 72, at step 130. Following this movement, the method returns to step 124 and monitor again determines the distance between piston 74 and solid support 108.

The cycle of steps 124, 126, 128 and 130 may repeat until piston 74 is within the allowable distance from solid support 108, which results in a "yes" response to the inquiry of step 126, which is indicated by step 132.

Once piston 74 is determined to be within the allowable distance from solid support 108, a determination is made as to whether system tolerances have been exceeded, at step 134. This determination preferably indicates whether excessive contact exists between piston 74 and solid support 108. For example, sensor 112 may comprise a strain gauge packaged in an appropriate moisture resistant enclosure and disposed along the bottom of piston 74. Sensor 112 may measure the degree of contact between piston 74 and solid support 108. Monitor 78 may be programmed to include a value corresponding to the maximum allowable deformation of the strain gauge of sensor 112. In that situation, step 134 may include comparing data obtained from sensor 112 to predetermined threshold deformation data stored in monitor 78.

Of course, other tolerances may be examined instead of, or in addition to, contact data provided by sensor 112. Examples of other tolerances include but are not limited to: pressure, temperature, pH, viscosity, density, voltage and resistance.

Step 136 queries whether system tolerances have been exceeded. If, for example, solid support 108 begins to expand in response to exposure to reagent R, the volume of solid support 108 will increase and its distance from piston 74 will decrease. Continued swelling may cause increased contact between solid support 108 and piston 74 that, if sufficient, may reduce the efficiency of the reactions within reactor 70 or cause other undesired consequences.

Accordingly, following receipt of data from sensor 112, monitor 78 determines whether the amount of contact between piston 74 and solid support 108 has exceed a permissible threshold. A "yes" response to this query is indicated at step 138. After a "yes" response is generated, monitor 78 sends a signal to actuator 76 to retract piston 74. In response, actuator 76 may activate gear 100 to engage teeth 102 and retract piston 74 from vessel 72 at step 140.

The method then returns to step 134 and another determination is made whether system tolerances are exceeded. Additional data is collected through sensor 112 and communicated to monitor 78 for comparisons, as described above.

Operation of this cycle may be understood by considering the example of solid support 108 swelling in response to reagent R. After one cycle of steps 134, 136, 138 and 140, piston 74 will have been retracted some amount. If it is determined that the contact is still outside the tolerance level, the cycle repeats, the piston is further retracted, and there is expected to be less contact pressure between piston 74 and solid support 108. This cycle repeats until the system tolerances are no longer exceeded. Preferably, the frequency at which this cycle occurs is selected so that the rate at which the piston moves is greater than the rate at which the solid support increases in volume.

Once a determination is made at step 136 that the system tolerances are not exceeded, a "no" response is generated at step 142. The method then proceeds to step 144 where it is determined whether the process is completed or whether a "terminate" signal has been received. The completion of the process may be predetermined and may occur, for example, after the last nucleotide is added to the oligonucleotide or after the oligonucleotide is cleaved from the solid support.

In contrast, a "terminate" signal may occur at an arbitrary point in the cycle and may, for example, be generated by monitor 78 in response to a determination that the pressure of reaction zone 88 exceeded the normal operational range. Likewise, a "terminate" signal may be inputted into the system by a user upon determination that the process should be aborted or "shut down."

In the event that the process is not completed and a "terminate" signal has not been received, the process continues from step 144 along the path beginning with a "no" response at step 146. The system then queries whether the stage is complete at step 148. For purpose of this example, this query addresses whether the stage of the process in which reagent R is added has been completed. This determination may be made based on different factors, including the time that the stage has been ongoing and/or data obtained from observation or from sensors 104 or 112.

If the stage of the process in which reagent R is added to solid support 108 is not complete, a "no" response is generated at step 150. In response, monitor 78 may send a signal to actuator 76 via wire 116 to maintain piston 74 in position. In response, actuator 76 may restrict movement of gear 100, thereby preventing the motion of piston 74, as indicated in step 152. The method then returns to step 124, where the distance between piston 74 and solid support 108 is determined.

It will be appreciated that although step 152 references maintaining piston 74 in position, it may be advantageous to have a dynamic system in which piston 74 is continually moving. In such instances, step 152 may be optional. Likewise, in other processes it may be desirable to move piston in a stepwise fashion. In those latter instances, it may be desirable to maintain piston 74 in a fixed position for a predetermined amount of time, for example 5 seconds, at step 152. The predetermined amount of time to maintain piston 74 in position may vary throughout the process and from stage to stage during the process.

Maintaining piston 74 in position may be advantageous for reactions that are expected to involve no change, or perhaps only a gradual change, in the volume of the solid support. As such, once piston 74 was properly positioned relative to solid support 108, the method would cycle through steps 124, 126, 132, 134, 136, 142, 144, 146, 148, 150 and 152. This cycle would involve ensuring that the piston continued to be in a proper position and that no system tolerances were exceeded.

In the event that the query at step 148 returns a response that the stage is complete, the process proceeds to step 154 indicating a "yes" response. From there, the method returns to step 122, where another stage may begin. For example, after completion of the stage in which reagent R is added to solid support 108, returning to step 122 would initiate the determination of the allowable distance between piston 74 and solid support 108 for the next reagent, such as reagent R'.

If at step 144, on the other hand, the process was complete or a "termination" signal was received, the method would proceed to step 156 indicative of a "yes" signal. The piston would then be retracted at step 158. This could be accomplished by an appropriate signal being sent by monitor 78 to actuator 76 directing the operation of gear 100 to retract piston 74 from vessel 72. The feedback process concludes at step 160.

Thus a feedback system is described in which piston 74 may be maintained within a predetermined distance from solid support 108, which also includes the zero distance condition that occurs when there is no headspace and piston 74 is in contact with solid support 108. This feedback method also provides a mechanism to prevent excessive contact between piston 74 and solid support 108 that may otherwise occur as solid support 108 expanded when exposed to a reagent and while in contact with piston 74. Hence, a zero headspace condition may be maintained during both the contraction and expansion of solid support 108.

Figure 5:
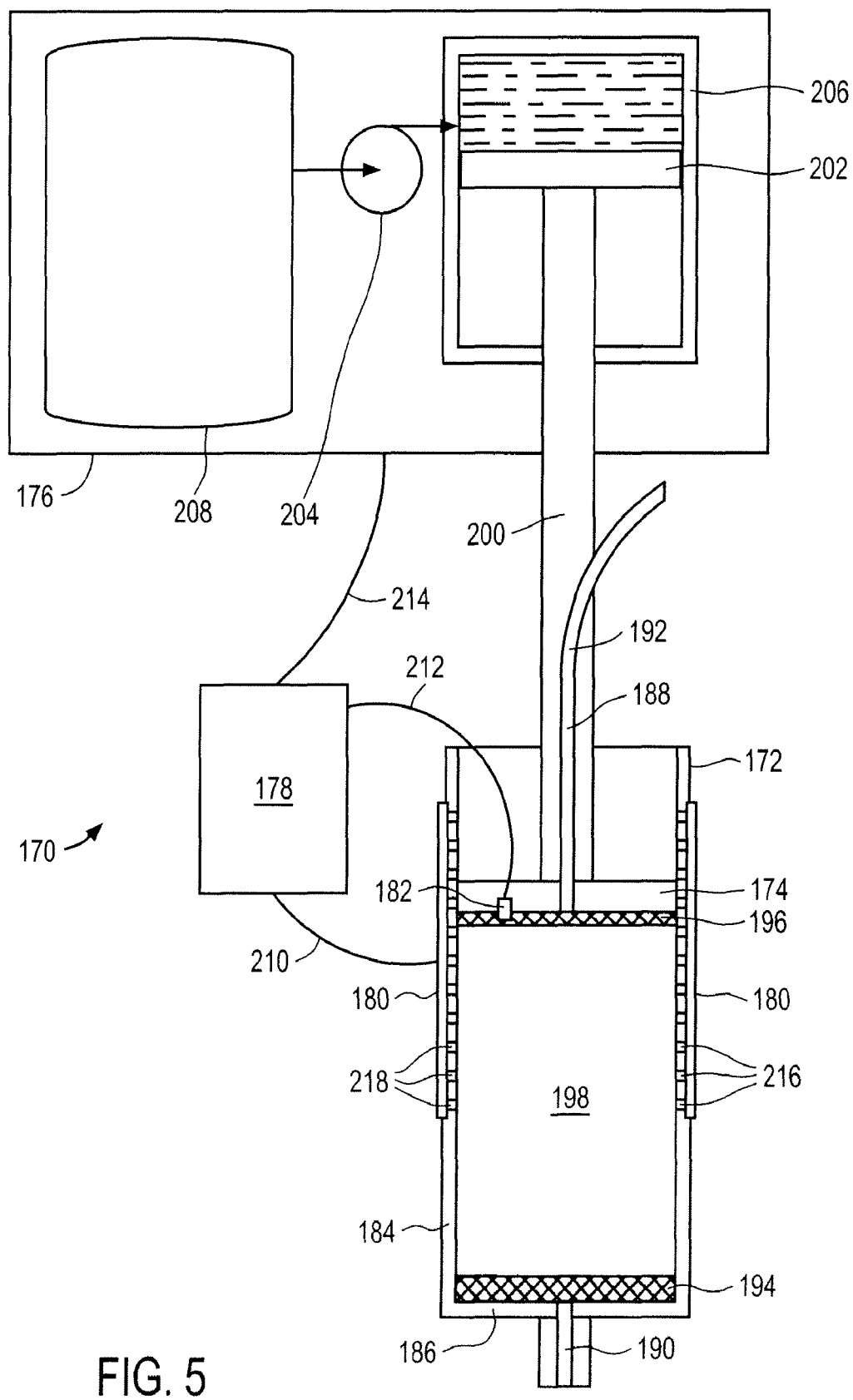
FIG. 5 is a schematic depiction of yet another embodiment of reactor in accordance with the present invention.

The embodiments of FIGS. 1 and 3 are intended to be exemplary, and are not intended to be limiting. Indeed, as noted in the description above, numerous arrangements and configurations of synthesizers are contemplated by this invention. As an example of yet another embodiment, reactor 170 is described with reference to FIG. 5.

Reactor 170 comprises vessel 172 in which piston 174 reciprocates. Movement of piston 174 may be provided by actuator 176 upon receipt of a signal from monitor 178. Monitor 178 receives data signals communicated by sensors 180 and sensor 182.

Vessel 172 comprises sidewall 184 and bottom 186, and also includes inlet 188 and outlet 190. Preferably, vessel 172 is configured to receive a fluid, such as a reagent, through inlet 188 via conduit 192, and is further configured to provide an exit for fluids via outlet 190. Vessel 172 may further comprise frit 194 disposed at or near bottom 186, wherein frit 194 is dimensioned to permit fluid to pass through, while preventing passage of matter having a predetermined cross-sectional area. While reactor 170 is adapted to receive fluids that are in liquid form, it will be appreciated that fluids may also include vapors and gases, including noble gases. Hence, as used herein, the term "fluid" is not intended to be limited to fluids in a liquid phase unless the context clearly demonstrates otherwise.

Piston 174 reciprocates within vessel 172. In a preferred embodiment, at least a portion of conduit 192 is disposed within piston 174. Moreover, in a preferred embodiment, conduit 192 contains a manifold that distributes the fluid in a substantially uniform manner when released into vessel 172. This uniform release optionally may be facilitated by frit 196 coupled to the bottom of piston 174.

Reaction zone 198 is bounded by the bottom of piston 174, sidewall(s) 184 and bottom 186. As piston 174 reciprocates within vessel 172, the volume of reaction zone 198 varies accordingly. Specifically, as piston 174 is extended into vessel 172, the volume of reaction zone 198 decreases. Likewise, as piston 174 is retracted from vessel 172, the volume of reaction zone 198 increases. In a preferred embodiment, reactor 170 is configured such that reactions take place within reaction zone 198. Reagents may be introduced into reaction zone through conduit 192, whereas byproducts of the reactions and excess reagent may be removed from reaction zone 198 via outlet 190. Solid support or other matter that may be desired for use in the reaction may be maintained within reaction zone 198 by appropriately dimensioning frit 194. Although reactor 170 is adapted for the synthesis of oligonucleotides, one of skill in the art will appreciate that this and other embodiments of the present invention are suitable for other applications, such as chromatography.

Actuator 176 controls movement of piston 174 by hydraulics. In particular, piston 174 includes shaft 200 that is coupled to hydraulic piston 202. Two way pump 204 selectively moves hydraulic fluid between hydraulic cylinder 206 and reservoir 208. As hydraulic fluid is pumped into hydraulic cylinder 206, piston 174 is extended into vessel 172 and volume of reaction zone 198 decreases. Likewise, as hydraulic fluid is pumped out of hydraulic cylinder 206 and into reservoir 208 by pump 204, piston 174 retracts from vessel 172 and the volume of reaction zone 198 increases.

In addition to being configured to allow for two-way pumping, pump 204 preferably may be controlled to vary the flow rate. It will be appreciated that these features may be met by a plurality of pumps instead of a single pump.

Monitor 178 receives data signals from sensors 180 and sensor 182 via wire 210 and wire 212, respectively. Monitor 178 communicates signals to actuator 176 via wire 214. It will be appreciated that various communications media may be utilized in place of wires 210, 212 or 214. For example, communication may be accomplished utilizing wireless radio signals, Bluetooth, Wi-Fi, fiber optics, or other known means.

Sensors 180 include transmitters 216 and receivers 218. Transmitters 216 emit a signal and receivers 218 are adapted to indicate a presence of that signal. Although transmitters 216 are depicted as disposed on substantially the opposite side of vessel 172 as receivers 218, many other configurations may be selected, including in a single series of alternating transmitters and receivers disposed in a line along sidewall 184. The signals that are transmitted may be a constant signal, may be a varied signal (such as variations in amplitude, frequency, or content) or may be a signal that is emitted in a pattern (such as a signal that is emitted in a pulsatile form).

The specific signals and types of transmitters 216 and receivers 218 may vary in different embodiments. For example, transmitters 216 may emit an optical signal, such as a light ray or a laser beam. Receivers 218 may be light sensors that respond to the presence of a light ray of a laser beam. In the event that only some of a series of receivers 218 detect the presence of an optical signal, the presence of a boundary between a fluid and a non-fluid may be indicated, such as the boundary between a liquid reagent and a solid support.

As another example, transmitters 216 may emit optical signals of a known frequency. Receivers 218 may be configured to determine the frequency of the received optical signals. In such as configuration, refraction of the light signals may cause a change in the frequency of the received light, thereby indicating the presence of a liquid. A series of such receivers 218 may provide information as to the location of a boundary between a liquid and a gas within vessel 172 based on the differences in received frequencies.

Still other embodiments may include transmitters 216 which emit an acoustic or radio signal. In some of those embodiments, receivers 218 may be configured to detect a distortion in the emitted signal. In some other of these embodiments, receivers 218 may be configured to detect a delay in the receipt of the emitted signal. These latter embodiments may be advantageous when transmitters 216 are adapted to emit signals as pulses, wherein the time that the signal is received by a plurality of receivers 218 varies to indicate differences in the matter between transmitters 216 and receivers 218.

In yet other embodiments, transmitters 216 emit an electrical signal and receivers 218 receive the electrical signal. A difference in the strength (measured in, for example, voltage) along a series of receivers 218 could indicate boundary conditions within vessel, such as the transition between a liquid and a gas.

Sensor 182 may be any type of sensor as described herein. For purposes of the embodiment described in accordance with FIG. 5, sensor 182 comprises a pressure sensor.

The general operation of reactor 170 is similar to that of reactor 70. As such, reactor 170 includes sensors 180 and 182 that provide feedback to monitor 178. Monitor 178 makes determinations as to what movement, if any, is appropriate for piston 174 based on the communications received from sensors 180 and 182. Monitor 178 communicates a command to actuator 176, which may cause piston 174 to retract, extend, or remain stationary as determined based on the information communicated.

The main differences between reactor 170 and reactor 70 involve actuator 176 and sensors 180 and 182. Lesser differences also exist, such as those involving vessel 172. Actuator 176 operates based on hydraulic forces, as described above, whereas actuator 76 employs gears 100 to impart motion. It should be clear from these differences that numerous suitable actuators are appropriate for use with the present invention. Other types of actuators include, but are not limited to, pneumatic actuators.

The other main difference between reactor 170 and reactor 70 involves sensors 180 and 182. In the embodiment of reactor 70, sensors 104 and 112 are coupled to piston 74. In contrast, in reactor 170, sensors 180 are coupled to vessel 172, such as being embedded in sidewall 184. One of skill in the art will appreciate that there are not only a range of suitable sensors that may be used with the present invention, but also that the placement of the sensors is not limited to the piston, but may also include the sidewall, bottom, inlet, outlet, and other locations of the vessel.

The operation of reactor 170 will be briefly described using an example where reactor 170 is used in the synthesis of an oligonucleotide. After a solid support is placed in vessel, sensor 180 may be used to detect a void, or a volume of space, above the solid support but below piston 174. Such a volume may be indicated by a portion of receivers 218 receiving a signal emitted from transmitters 216 that is different from the signals received (or where there is a detection of an absence of a signal) by the other receivers 218. For example, the uppermost receivers 218 may not receive an optical signal because piston 174 blocks the path of the signal between transmitters 216 and receivers 218. Likewise, the lowermost receivers 218 may not receive an optical signal because the solid support blocks the path of the signal between transmitters 216 and receivers 218. But, the portion of receivers 218 therebetween may receive a signal, which monitor 178 may determine is indicative of a volume of headspace between the solid support and piston 174.

In response, monitor 178 may send a command to actuator 176 to extend piston 174 into vessel 172. Monitor 178 may continue to send a command to advance piston 174 until there is an absence of signals received by receivers 218, indicating an absence of volume between the solid support and piston 174. Alternatively, it may be desirable to maintain a predetermined distance or volume between piston 174 and the solid support, and this may be accomplished through a feedback method similar to that described in accordance with FIG. 4 wherein the monitor maintains the piston in a position where a preselected number of receivers 218 receive a signal.

In the event that no headspace is desired, there may be a decreased ability for sensors 180 to detect the degree that swelling or other increase of volume of the solid support has occurred. Therefore, it may be advantageous to include sensor 182 which may be configured to detect, for example, pressure within reaction zone 198. In the event that sensor 182 detects a sufficient increase in pressure, monitor 178 may transmit a signal to actuator 176 to retract piston 174. In this manner, use of sensors 180 may be particularly useful in identifying negative volume changes of a solid support or other material, whereas sensor 182 may be particularly useful in identifying swelling or other positive changes in volume.

It will be appreciated that in some embodiments, a single sensor may be sufficient to detect both positive and negative volume changes of a solid support. For example, a contact sensor employing a strain gauge may be utilized to ensure that a piston is in contact with a solid support and may also be used to indicate whether that contact is increasing beyond a desired amount. In that manner, a single sensor could be appropriate for maintaining a zero headspace condition even when the solid support expands and contracts.

It will be understood by those skilled in the art that further modifications may be made to the embodiments described above that still fall within the scope of the invention. For example, a synthesizer may have a vessel containing a window or other transparency that allows visual observation of a portion of the reaction zone by a user. In such an embodiment, the user may manually enter into the monitor a command to raise or lower the piston using a keypad, toggle switch, or other input device. Such an embodiment would allow a user to manually control the position of the piston to limit or eliminate the headspace. Of course, such an embodiment may further include one or more sensors with outputs available to the user in order to provide the user with more information on which to base a decision as to whether, and how much, to move the piston.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed:

1. A reactor for synthesizing oligonucleotides comprising:
   a vessel configured to contain a solid support, the vessel having an inlet and an outlet;
   a piston operatively arranged to reciprocate with the vessel;
   an actuator coupled to the piston;
   a monitor configured to at least periodically adjust the actuator during a synthesis process to maintain the piston substantially in contact with the solid support; and
   at least one sensor located upstream of the vessel outlet and in communication with the vessel, each sensor configured to generate an output to the monitor;
   wherein the monitor adjusts the actuator according to the output from the at least one sensor or alternatively the monitor adjusts the actuator according to archival sensor output from a previous synthesis process.

2. The reactor of claim 1 wherein the vessel comprises a cylinder having a sidewall, top and bottom.

3. The reactor of claim 1 wherein the actuator comprises a hydraulic cylinder.

4. The reactor of claim 1 comprising a pressure sensor.

5. The reactor of claim 1 wherein the monitor further is configured to sense the output of a pressure sensor and adjust the actuator responsive to the output of the pressure sensor.

6. The reactor of claim 1 comprising a pressure sensor wherein the synthesis process comprises a series of steps, and the monitor is programmed to periodically adjust the actuator by discrete displacements corresponding to selected ones of the series of steps, archival sensor output and output from a pressure sensor.

7. The reactor of claim 1 wherein the synthesis process comprises a series of steps, and the monitor is programmed to adjust the actuator responsive to the output of each sensor wherein at least one sensor is selected from the group consisting of optical sensors, acoustic sensors, magnetic sensors, energy ray sensors, mechanical sensors and fiber-optic sensors and provides output corresponding to the detection of headspace adjacent to the solid support.

8. The reactor of claim 1 wherein each sensor is selected from the group consisting of optical sensors, acoustic sensors, magnetic sensors, energy ray sensors, mechanical sensors; and fiber-optic sensors.

9. A synthesizer comprising:
   a vessel configured to contain a granular polymeric material, the vessel having an inlet and an outlet, the vessel further configured to receive a fluid through the inlet;
   a piston operatively arranged to reciprocate with the vessel;
   an actuator coupled to the piston;
   a monitor configured to at least periodically adjust the actuator during a synthesis process to maintain the piston within a predetermined distance from the granular polymeric material; and
   at least one sensor located upstream of the vessel outlet and in communication with the vessel, each sensor configured to generate an output to the monitor;
   wherein the monitor adjusts the actuator according to the output from the at least one sensor or alternatively the monitor adjusts the actuator according to archival sensor output from a previous synthesis process.

10. The synthesizer of claim 9 wherein the vessel comprises a cylinder having a sidewall and a bottom.

11. The synthesizer of claim 9 wherein the actuator comprises a hydraulic cylinder.

12. The synthesizer of claim 9 comprising a pressure sensor.

13. The synthesizer of claim 9 wherein the monitor further is configured to sense the output of the pressure sensor and adjust the actuator responsive to the output of the pressure sensor.

14. The synthesizer of claim 9 comprising a pressure sensor wherein the synthesis process comprises a series of steps, and the monitor is programmed to periodically adjust the actuator by discrete displacements corresponding to selected ones of the series of steps, archival sensor output and output from a pressure sensor.

15. The synthesizer of claim 9 wherein the synthesis process comprises a series of steps, and the monitor is programmed to adjust the actuator responsive to the output of each sensor wherein at least one sensor is selected from the group consisting of optical sensors, acoustic sensors, magnetic sensors, energy ray sensors, mechanical sensors and fiber-optic sensors and provides output corresponding to the detection of headspace adjacent to the solid support.

16. The synthesizer of claim 9 wherein the sensor is selected from the group consisting of optical sensors, acoustic sensors, magnetic sensors, energy ray sensors, mechanical sensors and fiber-optic sensors.

* * * * *